United States Patent [19]

Oda et al.

[11] Patent Number: 5,258,529

[45] Date of Patent: Nov. 2, 1993

[54] PROCESS FOR PRODUCING PROPARGYLCARBINOL COMPOUNDS

[75] Inventors: Yoshiaki Oda; Sanshiro Matsuo, both of Toyonaka; Kenji Saito, Hirakata, all of Japan

[73] Assignee: Sumitomo Chemical Company, Limited, Osaka, Japan

[21] Appl. No.: 538,555

[22] Filed: Jun. 15, 1990

[30] Foreign Application Priority Data

Jun. 22, 1989 [JP] Japan .................................. 1-162098
Jul. 5, 1989 [JP] Japan .................................. 1-174997
Oct. 31, 1989 [JP] Japan .................................. 1-285570

[51] Int. Cl.$^5$ .................. C07D 333/16; C07D 317/44; C07C 33/28; C07C 33/46
[52] U.S. Cl. ...................... 549/78; 549/445; 549/497; 568/812; 568/813; 568/818; 568/873
[58] Field of Search ............... 568/873, 812, 813, 828; 549/78, 445, 497

[56] References Cited

U.S. PATENT DOCUMENTS 3,383,427 5/1968 Wolfe .................... 568/873

FOREIGN PATENT DOCUMENTS 0113107 7/1984 European Pat. Off. .
223592 9/1962 Fed. Rep. of Germany .
3724950 11/1988 Fed. Rep. of Germany .
1159181 6/1958 France .
0582764 11/1946 United Kingdom ................ 568/873
2188633 10/1987 United Kingdom ................ 568/873

OTHER PUBLICATIONS

Chemical Abstracts, 110:192517h Preparation of Propargyl Ketones as Intermediates for Prostaglandins . . . (EP 290,905).
J. Org. Chem. 49, 172 (1984).
Petrier et al. I "Zinc Mediated Allylations", etc. *Tetrahedron Letters,* vol. 26, No. 11, pp. 1449-1452 (1985).
Petrier et al II "Allylzinc Reagent Additions, etc" *J. Org Chem.* 1985, 50, pp. 910–912.
Franke et al., "Zur Herstellung der Acetylen-Binding, etc." *Angewandte Chemie,* 72 Jahrg. 1960, No. 12, pp. 391–400.
Schuda et al. "Elimination of Substituted Vinyl Halides, etc." *J. Org. Chem.,* 1982, 47, pp. 2484–2487.
Solomons et al. *Org. Chem,* 2nd Ed. John Wiley and Sons, New York, 1980, pp. 855–858.
March et al. *Advanced Org. Chem,* 3rd Ed, John Wiley and Sons, New York, 1985, pp. 914–916.

*Primary Examiner*—Allen J. Robinson
*Assistant Examiner*—P. O'Sullivan
*Attorney, Agent, or Firm*—Stevens, Davis, Miller & Mosher

[57] ABSTRACT

The present invention provides a process for producing a propargylcarbinol compound of formula (I):

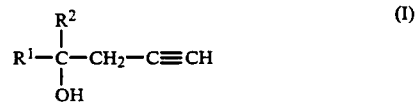

where $R^1$ and $R^2$ are as defined herein. The process comprises reacting a haloallycarbinol compound of formula (II) with a base. The present invention also relates to a process for producing the haloallylcarbinol compound. The above propargylcarbinol compound is useful as an intermediate for agrochemicals, pharmaceuticals, perfumes, resin monomers, and the like.

18 Claims, No Drawings

PROCESS FOR PRODUCING PROPARGYLCARBINOL COMPOUNDS

BACKGROUND OF THE INVENTION

1. Field of the Industry

The present invention relates to a process for producing propargylcarbinols useful as intermediates for agrochemicals, pharmaceuticals, perfumes, resin monomers, and the like.

2. Description of Related Prior Art

Propargylcarbinols have been heretofore produced by a Grignard reaction of propargyl bromide or propargyl chloride and a ketone or aldehyde compound.

Since, however, propargyl bromide and propargyl chloride are detonable or capable of monopropellant-type burning, in view of safety, the inhibition of the detonability is required in the industrial bulk use thereof (Fire Technology, Vol. 5, p. 100, 1969, etc.).

Therefore, the above-mentioned process is not always an industrially advantageous one.

SUMMARY OF THE INVENTION

The present inventors have found a process for producing a propargylcarbinol by dehalogenation with a base through a haloallylcarbinol, derived from a ketone compound or an aldehyde compound and 2,3-dihalo-1-propene, without use propargyl bromide or propargyl chloride.

The present invention relates to a haloallylcarbinol-producing reaction (step 1) for producing a haloallylcarbinol compound of the formula (II) (sometimes referred to as haloallylcarbinol Compound II hereinafter)

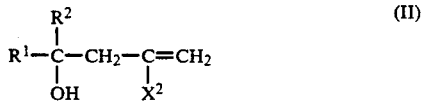

where $R_1$ and $R_2$ independently represent a hydrogen atom: a $C_1$–$C_{15}$ alkyl group which may be substituted with at least one member selected from the group consisting of halogen atoms, a hydroxyl group, a phenyl group, a phenoxy group, a phenyl or phenoxy group substituted with at least one member selected from the group consisting of halogen atoms and hydroxyl, alkoxy, phenoxy, dialkylamino and methylenedioxy groups, an aralkyloxy group, a dialkylamino group, an alkylthio group, a phenylthio group, a biphenyl group and a phenylalkyl group; a $C_2$–$C_{15}$ alkenyl group which may be substituted with at least one member selected from the group consisting of halogen atoms, a hydroxyl group, a phenyl group, a phenoxy group, a phenyl or phenoxy group substituted with at least one member selected from the group consisting of halogen atoms and hydroxyl, alkoxy, phenoxy, dialkylamino and methylenedioxy groups, a dialkylamino group, an alkylthio group, a phenylthio group, a biphenyl group and a phenylalkyl group; a $C_2$–$C_{15}$ alkynyl group which may be substituted with at least one member selected from the group consisting of halogen atoms, a hydroxyl group, a phenyl group, a phenoxy group, a phenyl or phenoxy group substituted with at least one member selected from the group consisting of halogen atoms and hydroxyl, alkoxy, phenoxy, dialkylamino and methylenedioxy groups, a dialkylamino group, an alkylthio group, a phenylthio group, a biphenyl group and a phenylalkyl group; a $C_3$–$C_{15}$ cycloalkyl group; a $C_4$–$C_{15}$ cycloalkenyl group; or a phenyl, naphthyl, furyl or thienyl group which may be substituted with at least one member selected from the group consisting of halogen atoms, and hydroxyl, alkyl, alkoxy, phenoxy, dialkylamino and methylenedioxy groups; or $R^1$ and $R^2$ together represent a $C_2$–$C_{15}$ alkylene or alkenylene chain; and $X^2$ represents a chlorine, bromine or iodine atom, with proviso that the carbon atoms in the 1-positions of $R^1$ and $R^2$ do not together form tertiary carbon atoms and that when one of $R^1$ and $R^2$ is the furyl group, the other does not represent a hydrogen atom: which comprises reacting a carbonyl compound of the formula (III) (referred to as Compound (III) hereinafter)

where $R^1$ and $R^2$ are as defined above, with a dihalopropene compound of the formula (IV) (referred to as Compound (IV) hereinafter)

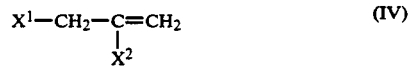

where $X^1$ and $X^2$ independently represent a chlorine, bromine or iodine atom in the presence of zinc and water.

Further, the present invention provides a process (step 2) for producing a propargylcarbinol compound (referred to as propargylcarbinol Compound (I) hereinafter) of the formula (I):

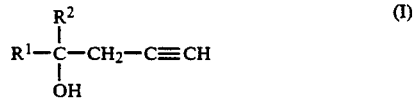

where $R^1$ and $R^2$ are as defined above, which comprises reacting haloallylcarbinol Compound (II) obtained in the above step 1 with a base.

An object of the present invention is to provide a process, with safety and industrial advantages for producing a propargylcarbinol compound useful as an intermediate for an agrochemical, pharmaceutical, perfume and resin monomer without using propargyl bromide or propargyl chloride.

PREFERRED EMBODIMENTS OF THE INVENTION

In the present invention, as preferred substituents $R^1$ and $R^2$, each of $R^1$ and $R^2$ independently of the other represents a hydrogen atom, a $C_1$–$C_{15}$ alkyl group which may be substituted with at least one member selected from the group consisting of halogen atoms and hydroxyl, phenyl, phenoxy, aralkyloxy, dialkylamino, alkylthio, phenylthio, biphenyl and phenylalkyl groups; a $C_3$–$C_9$ cycloalkyl or cycloalkenyl group; a $C_2$–$C_9$ alkenyl group which may be substituted with a phenyl group; a $C_2$–$C_6$ alkynyl group; or a phenyl, naphthyl, furyl or thienyl group which may be substituted with at least one member selected from the group consisting of halogen atoms and hydroxyl, alkyl, alkyloxy, phenoxy, dialkylamino and methylenedioxy groups. And, as more preferred substituents, each of $R^1$ and $R^2$ independently of the other represents a $C_1$-$C_{15}$ alkyl group which may be substituted with a phenyl a $C_2$-$C_9$ alkenyl group which may be substituted with a phenyl group; a $C_5$-$C_7$ cycloalkyl or cycloalkenyl group; a phenyl, naphthyl or thienyl group which may be substituted with at least one member selected from the group consisting of halogen atoms, $C_1$-$C_3$ alkyl, $C_1$-$C_3$ alkoxy, phenoxy and methylene-dioxy groups; or a hydrogen atom.

Each step of the present invention is detailed below.

Examples of Compound (III) used at the step 1 include $C_1$-$C_{15}$ linear aliphatic aldehydes such as formaldehyde, acetaldehyde, propionaldehyde, propenal, butanal, pentanal, hexanal, heptanal, 6-heptynal, decanal, dodecanal, tetradecanal, hexadecanal, etc.; branched or cyclic aliphatic aldehydes such as 2-methylpropionaldehyde, 4-methyl-1-pentanal, 2-methyl-2-pentenal, citral, cyclohexanecarbaldehyde, etc.; halogen-substituted aliphatic aldehydes such as 2-chlorohexanal, 3-bromoheptanal, etc.; hydroxyl-substituted aliphatic aldehydes such as 3-hydroxy-butanal, 6-hydroxyhexanal, etc.; aryl-containing aliphatic aldehydes such as phenylacetaldehyde, 2-phenylpropionaldehyde, biphenylacetaldehyde, cinnamic aldehyde, phenylpropynal, etc.; N,N-dialkylamino, alkylthio, arylthio, alkyloxy or aryloxy group-containing aliphatic aldehydes such as 2-(N,N-dimethylamino)propionaldehyde, 4-(N,N-diethylamino)-1-butanal, 4-methylthio-1-butanal, 4-phenylthio-1-butanal, 6-methoxy-1-hexanal, benzyloxyacetaldehyde, 6-phenoxy-1-hexanal, etc.; aromatic aldehydes such as benzaldehyde, o-tolaldehyde, m-tolaldehyde, p-tolaldehyde, p-methoxybenzaldehyde, 2,4-dimethoxybenzaldehyde, m-phenoxybenzaldehyde, p-chlorobenzaldehyde, o-bromobenzaldehyde, 2,4-dichlorobenzaldehyde, salicylaldehyde, 4-(N,N-dimethylamino)benzaldehyde, piperonal, etc.; thiophenecarbaldehydes such as 2-thiophenecarbaldehyde, 3-thiophenecarbaldehyde, etc.; linear, branched or cyclic alkyl, alkenyl or alkynyl-containing aliphatic ketones such as acetone, methyl ethyl ketone, methyl n-propyl ketone, methyl isopropyl ketone, methyl n-butyl ketone, methyl isobutyl ketone, methyl sec-butyl ketone, pinacolone, methyl pentyl ketone, methyl hexyl ketone, methyl heptyl ketone, methyl octyl ketone, methyl decyl ketone, methyl dodecyl ketone, methyl pentadecyl ketone, diethyl ketone, ethyl hexyl ketone, di-n-butyl ketone, cyclopentanone, cyclohexanone, cycloheptanone, cyclopentenone, methyl vinyl ketone, methyl 2-methyl-1-propenyl ketone, ethyl 2-butynyl ketone, etc.; halogen-containing aliphatic ketones such as chloromethyl ethyl ketone, bromomethyl ethyl ketone, etc.; oxygen, sulfur or nitrogen-containing ketones such as methyl 2-hydroxyethyl ketone, methyl methoxymethyl ketone, methyl phenoxymethyl ketone, methyl methylthiomethyl ketone, methyl phenylthiomethyl ketone, methyl N,N-dimethylaminomethyl ketone, etc.; optionally substituted benzene ring-containing ketones such as acetophenone, methyl p-tolyl ketone, methyl 2,4-dimethylphenyl ketone, methyl m-methoxyphenyl ketone, methyl m-phenoxyphenyl ketone, methyl 2,4-dichlorophenyl ketone, methyl p-bromophenyl ketone, ethyl o-hydroxyphenyl ketone, methyl p-(N,N-dimethylamino)phenyl ketone, etc.; arylalkyl, arylalkenyl or arylalkynyl-containing ketones such as methyl benzyl ketone, methyl 2-phenylethyl ketone, benzalacetone, etc.; and thienyl or furyl-containing ketones such as 2-acetylthiophene, 2-acetylfuran, etc.

Of the above Compounds (III), the aldehydes are referred to as aldehyde Compound (III-1) and the ketones as ketone Compound (III-2) hereinafter.

Examples of Compound (IV) include 2,3-dichloro-1-propene, 2,3-dibromo-1-propene, 2,3-diiodo-1-propene, 2-chloro-3-bromo-1-propene, 2-chloro-3-iodo-1-propene, 2-bromo-3-chloro-1-propene, 2-bromo-3-iodo-1-propene, 2-iodo-3-chloro-1-propene, and 2-iodo-3-bromo-1-propene.

Commercially available zinc in a variety of forms may be used as the zinc for the present reaction, and zinc in a powder or granular form is preferred. In particular, zinc in a powder form is more preferred.

The amount of the zinc to be used is 1 to 4 parts by mole, preferably 1.2 to 2 parts by mole, based on the aldehyde Compound (III-1) and 1 to 10 parts by mole, preferably 2 to 6 parts by mole, based on the ketone Compound (III-2).

The amount of water to be used is 1 to 24 parts by weight, preferably 2 to 9 parts by weight, based on Compound (III).

The amount of Compound (IV) to be used is usually 1 to 10 parts by mole based on the ketone Compound (III-2) and 1 to 4 parts by mole based on the aldehyde Compound (III-1).

The reaction of dehalogenation in the step 1 may be carried out in an organic solvent as required Examples of such an organic solvent are diethyl ether, tetrahydrofuran, dioxane, toluene, benzene, monochlorobenzene, ethylene dichloride, chloroform, ethyl acetate, methanol, etc.

The amount of the organic solvent used is not specially limited. However, it is preferably not more than 5 parts by weight, more preferably not more than 3 parts by weight based on the water.

The reaction temperature is in a range of 0 to 100° C., preferably 20 to 60° C.

The reaction time is usually 1 to 24 hours.

In addition, the reaction time can be shortened by adding a small amount of an acid, such as acetic acid, hydrochloric acid, hydrobromic acid, sulfuric acid, phosphoric acid, or the like.

Concerning the amount of the acid added in terms of a concentration in an aqueous solution thereof, when the aldehyde Compound (III-1) is used, the use of not more than 5% by weight of acetic acid or not more than 0.1% by weight of hydrochloric acid, hydrobromic acid, sulfuric acid or phosphoric acid is preferred. When the ketone Compound (III-2) is used, the use of not more than 20% by weight of acetic acid or not more than 1% by weight of hydrochloric acid, hydrobromic acid, sulfuric acid or phosphoric acid is preferred.

After the haloallylcarbinol Compound (II)-producing reaction is completed, the resultant mixture is treated in an ordinary manner, e.g. filtered, separated, concentrated or distilled, whereby the haloallylcarbinol Compound (II) can be obtained.

For step 2 for the production of the propargylcarbinol Compound (I) by dehydrohalogenation of the haloallylcarbinol Compound (II), a suitable combination of a base and a solvent is required.

Examples of the combination are:

(1) a polar aprotic solvent and an alkali metal hydroxide or alkali metal alkoxide, (2) a solvent selected from the group consisting of a mixed solvent of a hydrophobic hydrocarbon with water, a mixed solvent of a hydrophobic halogenated hydrocarbon with water, and water, and an alkali metal hydroxide in the presence of a phase transfer catalyst, and (3) an organic solvent and an alkali metal hydroxide or alkali metal alkoxide in the presence of a diamine.

Examples of the alkali metal hydroxide used in the reaction at the step 2 are sodium hydroxide, potassium hydroxide, etc. Examples of the alkali metal alkoxide are sodium methoxide, sodium ethoxide, potassium t-butoxide, etc.

Examples of the polar aprotic solvent used in the above combination (1) are acetonitrile, N,N-dimethylacetamide, N,N-dimethylformamide, N-methyl-2-pyrrolidone, dimethylsulfoxide, and hexamethylphosphoric acid triamide, etc.

Examples of the hydrophobic hydrocarbon and the hydrophobic halogenated hydrocarbon used in the above combination (2) are pentane, hexane, benzene, toluene, xylene, methylene chloride, chloroform, ethylene dichloride, and monochlorobenzene, etc.

Examples of the phase transfer catalyst are organic quaternary ammonium salts such as tetra-n-butylammonium bromide, tetra-n-butylammonium chloride, tetra-n-pentylammonium bromide, tetra-n-pentylammonium iodide and benzyltriethylammonium chloride, and polyethylene glycols having a molecular weight of 200, 300, 600 or the like.

Examples of the organic solvent used in the above combination (3) are ethyl ether, tetrahydrofuran, dioxane, diglyme, triglyme, triethylamine, pyridine and such solvents as are specified concerning the combinations (1) and (2).

Examples of the diamine are ethylenediamine, N,N,N',N'-tetramethylethylenediamine, 1,2-diaminopropane, 1,3-diaminopropane, 1,4-diaminobutane, 1,6-diaminohexane, 1,8-diazabicyclo[5,4,0]undec-7-ene, 1,5-diazabicyclo[4,3,0]non-5-ene, and 1,4-diazabicyclo[2,2,2]octane. When ethylenediamine, 1,2-diaminopropane or 1,3-diaminopropane is used, the solvent is not necessarily required.

The amount of the base is usually 1 to 10 parts by mole, preferably 1 to 4 parts by mole, based on the haloallylcarbinol Compound (II).

The amount of the solvent other than water is not specially limited. However, it is usually 0.1 to 20 parts by weight based on the haloallylcarbinol Compound (II).

When water is used, its amount is usually 1 to 5 parts by weight based on the alkali metal hydroxide.

The amount of the phase transfer catalyst in the combination (2) is 0.5 to 10 parts by mole, preferably 0.5 to 5 parts by mole, based on the haloallylcarbinol Compound (II).

The amount of the diamine in the combination (3) is usually 1 to 20 parts by mole, preferably 1 to 15 parts by mole based on the haloallylcarbinol Compound (II).

The reaction temperature of the above step 2 is usually in a range of $-20$ to $100°$ C., preferably 0 to $60°$ C.

The reaction time is not specially limited, and the reaction can be quenched when the haloallylcarbinol Compound (II), a starting material, is not detected any longer.

After the reaction, the resultant mixture is treated, i.e. by filtering, addition of water, extraction, separation, concentration or distillation, whereby the propargylcarbinol Compound (I) can be obtained.

In the present invention, the formation of a by-product, an allene compound of the formula (V) which is an isomer of the propargylcarbinol Compound (I), is low, and the propargylcarbinol Compound (I) can be obtained highly selectively.

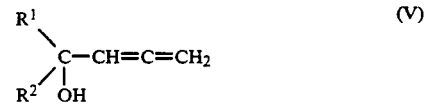

(V)

The propargylcarbinol Compound (I) obtained according to the above-detailed process is useful as a compound shown below or as an intermediate therefor.

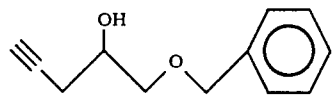  Antibacterials, Perfumes

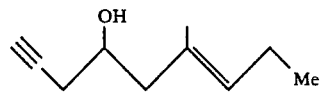  Insecticides, Acaricides

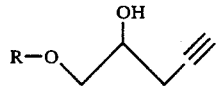  Pharmaceuticals, Agrochemicals, Cosmetics (R: Benzyl etc.)

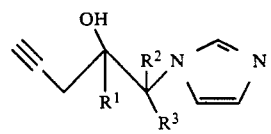  Candidiasis

-continued
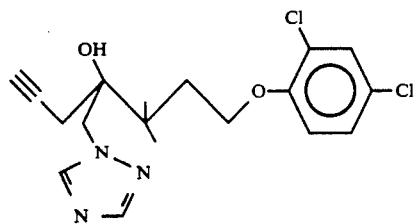 Fungicides
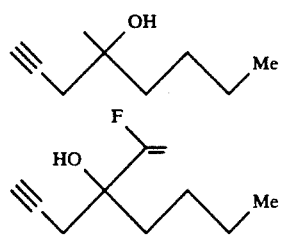 ω chain of prostaglandin
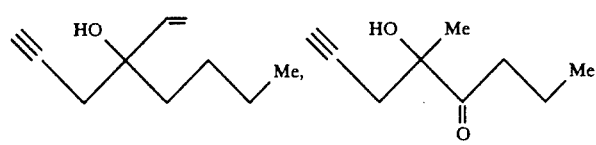 ditto
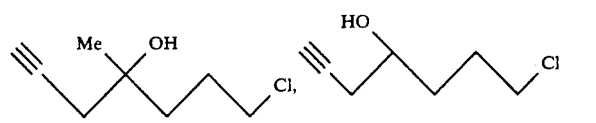 ditto
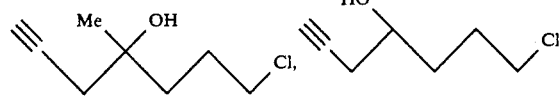
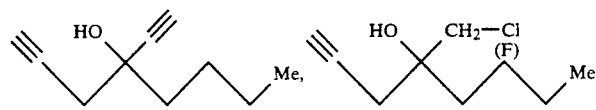 ditto
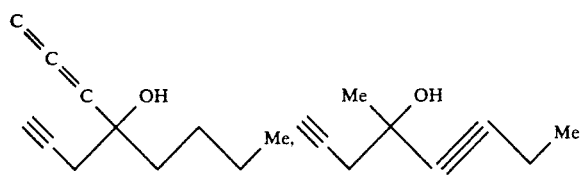
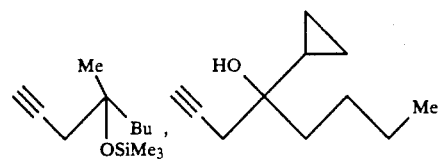
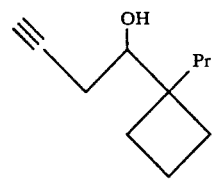
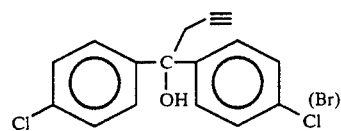 Fungicides -continued
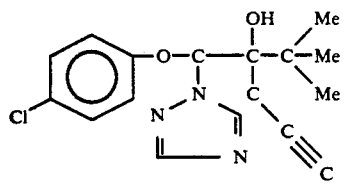 ditto
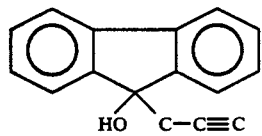 Antimycotic
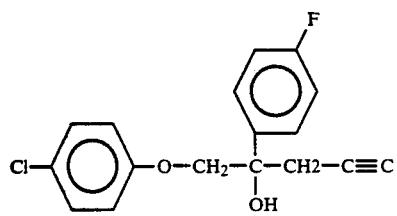 ditto
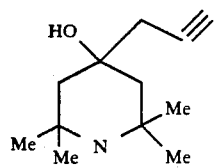 Radical catcher
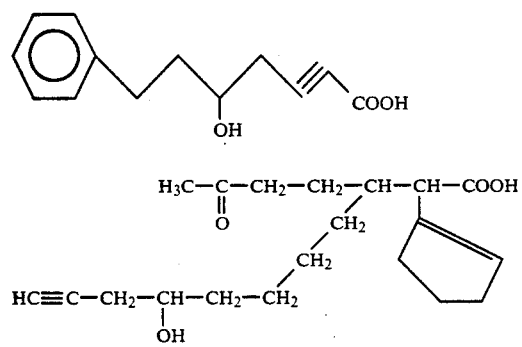 Pharmaceuticals
Bactericides
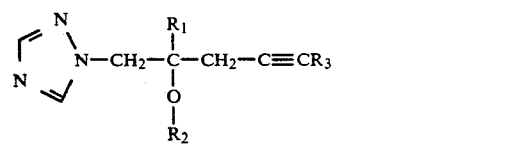 Plant growth regulators
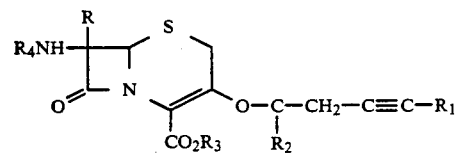 Cephalosporins
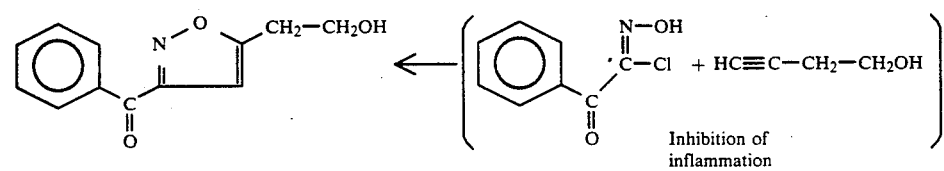
Inhibition of inflammation

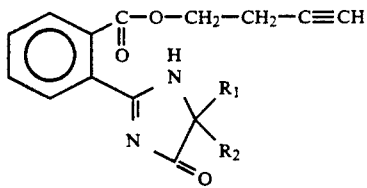 Plant growth regulator

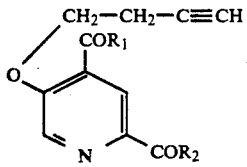 Pharmaceuticals

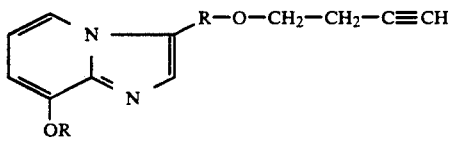 Gastric antiulcer

The present invention is explained further in detail hereinbelow by reference the Examples.

EXAMPLE 1

45.23 Grams of 2,3-dichloro-1-propene were added dropwise to a mixture of 20.00 g of cyclohexanone, 60 g of toluene, 60 g of water and 26.65 g of zinc powder at 35° C., and after the addition, the resultant mixture was maintained at the same temperature for 5 hours. After the reaction was completed zinc-derived in solubles were filtered off, and the resultant filtrate was separated. The organic phase thereof was washed with a 7% sodium carbonate aqueous solution, and dried over magnesium sulfate. The desiccant was filtered off, and the resultant toluene solution was concentrated under reduced pressure to give 32.75 g of 1-(2'-chloroallyl-1-cyclohexanol; $n_D^{20}=1.495$, EI-MS m/e 156 (M-H$_2$O$^+$), 158 (M-H2O+2$^+$).

10.00 Grams of the 1-(2'-chloroallyl)-1-cyclohexanol obtained above were dissolved in 94 g of N,N-dimethylformamide, and 9.65 g of potassium hydroxide in a flake form were added. The mixture was stirred at room temperature for 6 hours, and neutralized with a 20% acetic acid aqueous solution. The resultant mixture was subjected to extraction with toluene. The toluene phase was washed with water and dried over magnesium sulfate. The desiccant was filtered off and the toluene was distilled off under reduced pressure to give 7.68 g of 1-propargyl-1-cyclohexanol; m.p.=53–54° C., FI-MS m/e 138(M$^+$) (Propargyl compound/allene compound=100.0/0.0), bp 48–49° C./1 mmHg.

FI-MS m/e 138 (M$^+$), 120 (M-H$_2$O$^+$).

IR (neat) 3440, 3320, 2120 cm$^{-1}$.

$^1$H-NMR (CDCl$_3$, internal standard TMS), δ1.25–1.70 (m, 10H), 1.83 (2, 1H), 2.08 (t, 1H, J=2.6 Hz), 2.36 (d, 2H, J=2.6 Hz).

EXAMPLE 2

45.23 Grams of 2,3-dichloro-1-propene were added dropwise to a mixture of 20.00 g of methyl 2-methyl-1-propenyl ketone, 60 g of toluene, 60 g of water and 26.65 g of zinc powder at 35° C., and after the addition, the resultant mixture was maintained at the same temperature for 5 hours. After the reaction was completed zinc-derived insolubles were filtered off, and the filtrate was separated. The organic phase was washed with 7% sodium carbonate aqueous solution and dried over magnesium sulfate. The desiccant was filtered off and the toluene was distilled off under reduced pressure. The resultant oily substance was purified by silica gel column chromatography to give 31.11 g of 2-chloro-4,6-dimethyl-1,5-heptadien-4-ol; $n_D^{25}=1.474$, FI-MS m/e 174(M), 176(M+2).

10.00 Grams of the 2-chloro-4,6-dimethyl-1,5-heptadien-4-ol obtained above were dissolved in 94 g of N,N-dimethylformamide, and 9.65 g of potassium hydroxide in a flake form were added. The resultant mixture was stirred at room temperature for 4 hours and neutralized with a 20% acetic acid aqueous solution, and the resultant mixture was subjected to extraction with toluene. The toluene phase was washed with water and then dried over magnesium sulfate. The desiccant was filtered off, and then the toluene was distilled off under reduced pressure. The resultant oily substance was purified by silica gel column chromatography to give 6.32 g of methyl 2-methylallylpropargylcarbinol; $n_D^{25}=1.496$, FI-MS m/e 138 (M$^+$) (Propargyl compound/allene compound=100.0/0.0).

EXAMPLE 3

33.26 of 2,3-dichloro-1-propene were added dropwise to a mixture of 20.00 g of acetophenone, 40 g of ethylene dichloride, 60 g of 5% acetic acid and 19.52 g of zinc powder at 50° C., and the resultant mixture was allowed to react at the same temperature for 10 hours. After the reaction was completed, zinc-derived insolubles were filtered off, and the resultant filtrate was separated. The organic phase was washed with 7% sodium carbonate aqueous solution and dried over magnesium sulfate. The desiccant was filtered off, and the ethylene dichloride was distilled off under reduced pressure. The resultant oily substance was purified by silica gel column chromatography to give 22.24 g of 2-chloro-4-phenyl-1-penten-4-ol; $n_D^{25}=1.536$, FI-MS m/e 178(M-H$_2$O$^+$), 180 (M-H$_2$O+2$^+$).

20.00 Grams of the 2-chloro-4-phenyl-1-penten-4-ol were dissolved in 50 g of toluene, and 30.5 g of a 40% sodium hydroxide aqueous solution and 65.57 g of tetran-butylammonium bromide were added. The mixture was allowed to react at 50° C. for 30 hours, and then was subjected to separation. The organic phase was washed with water, and the toluene was distilled off under reduced pressure. The resultant oily substance was purified by silica gel column chromatography to give 11.37 g of 4-phenyl-1-pentyn-4-ol; $n_D^{21}=1.537$ FI-MS m/e 160(M+) (Propargyl compound/allene compound 100.0/0.0).

EXAMPLE 4

47.53 Grams of 2,3-dibromo-1-propene were added dropwise to a mixture of 15.00 g of 2-acetylthiophene, 30 g of toluene, 50 g of 0.01% hydrochloric acid and 15.55 g of zinc powder at 45° C, and the mixture was allowed to react at the same temperature for 9 hours. After the reaction was completed, zinc-derived insolubles were filtered off, and the resultant filtrate was subjected to separation. The organic phase was washed with a 7% sodium carbonate aqueous solution, and the toluene was distilled off under reduced pressure. The resultant oily substance was purified by silica gel column chromatography to give 15.55 g of α-(2-bromo-2-propenyl)-α-(2-thiophene)ethanol; $n_D^{25}=1.539$, FI-MS m/e 246(M), 248(M+2).

12.00 Grams of the α-(2-bromo-2-propenyl)-α-(2-thiophene)ethanol obtained above were dissolved in 108 g of N-methyl-2-pyrrolidone, and 6.30 g of sodium methylate were added. The mixture was allowed to react at 40° C. for 12 hours and then neutralized with concentrated hydrochloric acid, and insolubles were filtered off. An oily substance obtained by concentrating the filtrate under reduced pressure was purified by silica gel column chromatography to give 5.77 g of α-propargyl-α-(2-thiophene)ethanol; $n_D^{25}=1.516$, FI-MS m/e 166(M) (Propargyl compound/allene compound 100.0/0.0).

EXAMPLE 5

5.00 Grams of 2-iodoallylmethyl-o-naphthylcarbinol were dissolved in 50 g of dimethylformamide, and 1.18 g of sodium hydroxide in a flake form were added. The resultant mixture was stirred at room temperature for 8 hours. After the reaction was completed, the reaction mixture was neutralized with concentrated hydrochloric acid, insolubles were filtered off, and the remaining filtrate was concentrated under reduced pressure. The concentration residue was subjected to extraction with toluene, and washed with a 7% sodium carbonate aqueous solution. Then, the toluene was distilled off under reduced pressure to give 2.77 g of methyl-α-naphthyl-propargylcarbinol; $n_D^{25}=1.5141$, FI-MS m/e 210 (M) (Propargyl compound/allene compound 100.0/0.0).

EXAMPLE 6

58.30 Grams of 2,3-dichloro-1-propene were added dropwise to a mixture of 30.00 g of heptanol, 90 g of toluene, 120 g of water and 34.35 g of zinc powder at 45° C., and then, the resultant mixture was allowed to react at the same temperature for 10 hours. After the reaction finished, zinc-derived insolubles were filtered off, and the resultant filtrate was subjected to separation. The organic phase was washed with a 7% sodium carbonate aqueous solution and then dried over sodium sulfate. The desiccant was filtered off, and then the toluene was distilled off under reduced pressure to give 47.14 g of 2-chloroallyl-n-hexyl-carbinol. The results were as follows.

Yield 94.1%.
bp 74–75° C./0.7 mmHg
$n_D^{20}$ 1.460.
FI-MS m/e 190 (M+), 192 (M+2+).
IR (neat) 3370, 1640 $cm^{-1}$,
$^1$H-NMR (CDCl$_3$, internal standard TMS), δ0.89 (m, 3H), 1.30–1.74 (m, 10H), 1.82 (brs, 1H), 2.38–2.52 (m, 2H), 3.93 (m, 1H), 5.25 (m, 1H), 5.28 (d, 1H, J=1.3 Hz).

20.00 Grams of the 2-chloroallyl-n-hexylcarbinol obtained above were dissolved in 200 g of N,N-dimethylformamide, and 8.39 g of sodium hydroxide in a flake form were added. The resultant mixture was stirred at 25° C. for 10 hours. After the reaction was completed the reaction mixture was neutralized with concentrated hydrochloric acid, and insolubles were filtered off. After the filtrate was concentrated under reduced pressure, the concentration residue was subjected to extraction with toluene, washed with a 7% sodium carbonate aqueous solution and then dried over sodium sulfate. The desiccant was filtered off, and the toluene was distilled off. The resultant oily substance was distilled under reduced pressure to give 15.70 g of n-hexylpropargylcarbinol. The results were as follows.

Yield 97.0% (propargyl compound/allene compound 98.0/2.0).
bp 66.5–68.5° C./0.8 mmHg.
$n_D^{21}$ 1.449.
FI-MS m/e 154 (M+), 136 (M-H$_2$O+).
IR (neat) 3380, 3310, 2120 $cm^{-1}$,
$^1$H-NMR (CDCl$_3$, internal standard TMS),
δ0.89 (m, 3H), 1.29–1.56 (m, 10H), 2.06 (t, 1H, J=2.6 Hz), 2.20 (d, 1H, J=4.9 Hz), 2.27–2.47 (m, 2H), 3.75 (m, 1H).

EXAMPLE 7

125.40 Grams of 2,3-dichloro-1-propene were added dropwise to a mixture of 60.00 g of benzaldehyde, 180 g of toluene, 240 g of 5% acetic acid and 73.88 g of zinc powder at 45° C., and then the mixture was allowed to react at the same temperature for 3 hours. After the reaction was completed zinc-derived insolubles were filtered off, and the resultant filtrate was subjected to separation. The organic phase was washed with a 7% sodium carbonate aqueous solution and dried over sodium sulfate. The desiccant was filtered off, and then the toluene was distilled off under reduced pressure to give 98.23 g of 2-chloroallylphenylcarbinol. The results were as follows.

Yield 95.2%.
bp 103–104° C./2.5 mmHg.
$n_D^{19}$ 1.543.
FI-MS m/e 182 (M+), 184 (M+2+).
IR (neat) 3390, 1640 $cm^{-1}$.
$^1$H-NMR (CDCl$_3$, internal standard TMS), δ2.22 (brs, 1H), 2.60–2.80 (m, 2H), 5.00 (dd, 1H, J=8.9, 4.3 Hz), 5.20 (d, 1H, J=1.0 Hz), 5.26 (d, 1H, J=1.3 Hz), 7.23–7.38 (m, 5H).

40.00 Grams of the 2-chloroallylphenylcarbinol obtained above were disolved in 400 g of N,N-dimethylformamide, and 17.52 g of sodium hydroxide in a flake form were added. The mixture was stirred at 25° C. for 7 hours. After the reaction was completed the reaction mixture was neutralized with concentrated hydrochloric acid, and insolubles were filtered off. The filtrate was concentrated under reduced pressure, and then the concentration residue was subjected to extraction with toluene, washed with a 7% sodium carbonate aqueous solution and dried over sodium sulfate. The desiccant was filtered off, and the toluene was distilled off under reduced pressure. The resultant oily substance was distilled under reduced pressure to give 30.84 g of phenyl-propargylcarbinol. The results were as follows.

Yield 96.3% (propargyl compound/allene compound 93.2/6.8).

bp 74–76° C./0.5 mmHg.

$n_D^{20}$ 1.546.

FI-MS m/e 146 (M+), 128 (M-H$_2$O+).

IR (neat) 3390, 3300, 2120 cm$^{-1}$, $^1$H-NMR (CDCl$_3$, internal standard TMS), δ2.06 (t, 1H, J=2.6 Hz), 2.47 (d, 1H, J=3.6 Hz), 2.63 (dd, 2H, J=6.3, 2.6 Hz), 4.85 (m, 1H), 7.24–7.40 (m, 5H).

EXAMPLE 8

47.50 Grams of 2,3-dichloro-1-propene were added dropwise to a mixture of 20.00 g of crotonaldehyde, 40 g of ethylene dichloride, 60 g of 3% acetic acid and 18.65 g of zinc powder at 40° C., and the resultant mixture was allowed to react at the same temperature for 5 hours. After the reaction was completed, zinc-derived insolubles were filtered off, and the resultant filtrate was subjected to separation. The organic phase was washed with a 7% sodium carbonate aqueous solution and dried over magnesium sulfate. The desiccant was filtered off, and the ethylene dichloride was distilled off under reduced pressure to give 37.15 g of 2-chloro-1,5-heptadien-4-ol; $n_D^{25}$=1.471, FI-MS m/e 146(M+), 148(M+2+).

20.00 Grams of the 2-chloro-1,5-heptadien-4-ol obtained above were dissolved in 50 g of toluene, and 40.9 g of a 40% sodium hydroxide aqueous solution and 87.94 g of tetra-n-butylammonium bromide were added. The resultant mixture was allowed to react at 50° C. for 24 hours and then separated, and the organic phase was washed with water. The toluene was distilled off under reduced pressure. The resultant oily substance was purified by silica gel column chromatography to give 10.72 g of hept-5-en-1-yn-4-ol; $n_D^{25}$=1.493, FI-MS m/e 110(M+), propargyl compound/allene compound 94.0/6.0.

EXAMPLE 9

49.93 Grams of 2,3-dibromo-1-propene were added dropwise to a mixture of 20.00 g of phenylacetaldehyde, 40 g of toluene, 60 g of 0.01% hydrochloric acid and 16.33 g of zinc powder at 30° C., and the mixture was allowed to react at the same temperature for 3 hours. After the reaction was completed zinc-derived insolubles were filtered off, and the resultant filtrate was separated. The organic phase was washed with a 7% sodium carbonate aqueous solution, and the toluene was distilled off under reduced pressure. The resultant oily substance was purified by silica gel column chromatography to give 24.01 g of 2-bromo-5-phenyl-1-penten-4-ol; $n_D^{25}$=1.536, FI-MS m/e 240(M+), 242(M+2+).

20.00 Grams of the 2-bromo-5-phenyl-1-penten-4-ol obtained above were dissolved in 160 g of N-methyl-2-pyrrolidone, and 11.20 g of sodium methylate were added. The mixture was allowed to react at 30° C. for 14 hours, and then was neutralized with concentrated hydrochloric acid. Insolubles were filtered off, and the filtrate was concentrated under reduced pressure. The resultant oily substance was purified by silica gel column chromatography to give 9.96 g of 5-phenyl-1-pentyn-4-ol, $n_D^{25}$=1.519, FI-MS m/e 160(M+), propargyl compound/allene compound 97.9/2.1.

EXAMPLE 10

19.5 Grams of 2-chloroallylphenylcarbinol were dissolved in 100.0 g of 1,3-diaminopropane, and 9.2 g of sodium methylate were added. The mixture was allowed to react at 30° C. for 16 hours. Then, the reaction mixture was neutralized with concentrated hydrochloric acid, and insolubles were filtered off. The filtrate was concentrated under reduced pressure, and the resultant oily substance was purified by silica gel column chromatography to give 12.6 g of phenylpropargylcarbinol, $n_D^{20}$=1.546, FI-MS m/e 146(M+), propargyl compound/ allene compound=93.0/7.0.

EXAMPLE 11

5.00 Grams of 2-iodoallyl-α-naphthylcarbinol were disolved in 50 g of dimethylformamide, and 1.23 g of sodium hydroxide in a flake form were added. The mixture was stirred at room temperature for 6 hours. After the reaction was completed the reaction mixture was neutralized with concentrated hydrochloric acid, insolubles were filtered off, and the filtrate was concentrated under reduced pressure. The concentration residue was subjected to extraction with toluene and washed with a 7% sodium carbonate aqueous solution, and then the toluene was distilled off under reduced pressure to give 2.78 g of α-naphthylpropargylcarbinol; $n_D^{25}$=1.549, FI-MS m/e 196(M+).

EXAMPLES 12–34

Propargylcarbinol compounds (I) were produced from haloallylcarbinol compounds (II) shown in Table 1 according to conditions described in Example 11. The results are shown in Table 1.

TABLE 1

| Example | Haloallylcarbinol Name | Amount (g) | Base Name | Amount (g) | Solvent Name | Amount (g) | Reaction temperature (°C.) | Reaction time (hr) |
|---|---|---|---|---|---|---|---|---|
| 12 | 2-Chloroallyl-isopropylcarbinol | 30.00 | NaOH | 12.11 | Ethylenediamine | 121.28 | 25 | 8.5 |
| 13 | n-Butyl-2-chloro-allylcarbinol | 15.00 | " | 7.36 | Dimethylformamide | 150 | 40 | 4 |
| 14 | 2-Chloroallyl-n-pentylcarbinol | " | " | 6.80 | Dimethylformamide | " | " | " |
| 15 | 2-Chloroallyl-n-hexylcarbinol | 10.00 | KOH | 8.81 | Dimethylformamide | 100 | 25 | 6 |
| 16 | 2-Chloroallyl-cyclohexylcarbinol | 20.00 | NaOH | 8.48 | Dimethylformamide | 200 | " | 10 |
| 17 | 10-Chloro-2,6-dimethyl-2,6,10-undecatrien-8-ol | " | " | 6.99 | Dimethylformamide | " | " | " |
| 18 | 5-Chloro-2-phenyl-5-hexen-3-ol | " | " | 7.59 | Dimethylformamide | " | 20 | 8 |

TABLE 1-continued

| | Name | | | | | | | |
|---|---|---|---|---|---|---|---|---|
| 19 | trans-5-Chloro-1-phenyl-1,5-hexadien-3-ol | 24.43 | " | 9.37 | Dimethylformamide | 244.3 | 25 | " |
| 20 | 2-Chloroallylphenylcarbinol | 40.00 | NaOH | 17.52 | Dimethylformamide | 400 | 25 | 7 |
| 21 | 2-Chloroallyl-p-tolylcarbinol | 15.00 | " | 6.12 | Dimethylformamide | 150 | 40 | 4 |
| 22 | 2-Chloroallyl-p-methoxyphenylcarbinol | " | " | 5.64 | Dimethylformamide | " | " | " |
| 23 | 2'-Chloroallyl-3,4-methylenedioxyphenyl-carbinol | 23.00 | " | 8.12 | Dimethylformamide | 230 | 25 | 10 |
| 24 | 2'-Chloroallyl-3,4-methylenedioxyphenyl-carbinol | " | " | " | Dimethylformamide | " | 40 | 4 |
| 25 | 2-Chloroallyl-p-chlorophenylcarbinol | " | " | 8.47 | Dimethylformamide | " | 25 | 10 |
| 26 | 2-Chloroallyl-p-chlorophenylcarbinol | " | " | " | Dimethylformamide | " | 40 | 3 |
| 27 | 2'-Chloroallyl-2,4-dichlorophenyl-carbinol | 15.00 | " | 4.76 | Dimethylformamide | 150 | 25 | 12 |
| 28 | 2-Chloroallyl-2-thienylcarbinol | 20.00 | " | 8.48 | Dimethylformamide | 200 | " | " |
| 29 | 1-(2'-Chloroallyl)-cyclohexan-1-ol | 20.00 | NaOH | 8.57 | Dimethylformamide | 200 | 25 | 10 |
| 30 | 2-Chloro-4-methyl-1-octen-4-ol | " | " | 9.06 | Dimethylformamide | " | " | 12 |
| 31 | 5-Chloro-3-methyl-1-phenyl-5-hexen-3-ol | " | " | 7.12 | Dimethylformamide | " | " | " |
| 32 | 5-Chloro-3-methyl-1-phenyl-1,5-hexadien-3-ol | 18.49 | " | 6.64 | Dimethylformamide | 184.9 | " | " |
| 33 | 4-Chloro-2-phenyl-4-penten-2-ol | 20.00 | " | 8.14 | Dimethylformamide | 200 | " | 5 |
| 34 | 5-(2'-Chloroallyl)-nonan-5-ol | 17.50 | " | 6.40 | Dimethylformamide | 175 | " | 12 |

| | Propargylcarbinol (I) | | | |
|---|---|---|---|---|
| Name | Yield (%) | Propargyl compound/allene compound | $n_D$ | MS |
| Isopropylproparagyl-carbinol | 94.9 | 97.7/2.3 | 1.447 (20° C.) | FI-MS 112(M$^+$) |
| n-Butylpropargyl-carbinol | 95.9 | 87.5/12.5 | 1.447 (24° C.) | FI-MS 126(M$^+$) |
| n-Pentylpropargyl-carbinol | 96.6 | 87.6/12.4 | 1.449 (24° C.) | FI-MS 140(M$^+$) |
| n-Hexylpropargyl-carbinol | 94.9 | 90.6/9.4 | | • |
| Cyclohexylpropargyl-carbinol | 99.0 | 99.5/0.5 | 1.486 (24° C.) | FI-MS 152(M$^+$) |
| 2,6-Dimethylundeca-2,6-dien-10-yn-8-ol | " | Unknown | 1.488 (21° C.) | FI-MS 192(M$^+$) |
| 2-Phenyl-5-hexyn-3-ol | 93.3 | 100.0/0.0 | mp 64° C. | FD-MS 174(M$^+$) |
| trans-1-Phenyl-hexa-1-en-5-yn-3-ol | 92.9 | 98.2/1.8 | 1.573 (21° C.) | FD-MS 172(M$^+$) |
| Phenylpropargyl-carbinol | 96.3 | 93.2/6.8 | | |
| Propargyl-p-tolylcarbinol | 93.9 | 83.9/16.1 | 1.543 (24° C.) | FD-MS 160(M$^+$) |
| p-Methoxyphenyl-propargylcarbinol | 98.3 | 84.2/15.8 | 1.553 (24° C.) | FD-MS 176(M$^+$) |
| 3,4-Methylenedioxy-phenylpropargyl-carbinol | 97.0 | 91.6/8.4 | 1.565 (21° C.) | FD-MS 190(M$^+$) |
| 3,4-Methylenedioxy-phenylpropargyl-carbinol | 96.5 | 85.2/14.8 | | |
| p-Chlorophenyl-propargylcarbinol | 99.5 | 92.1/7.9 | 1.557 (21° C.) | FI-MS 180(M$^+$) 182(M + 2$^+$) |
| p-Chlorophenyl-propargylcarbinol | 95.1 | 86.1/13.9 | | |
| 2,4-Dichlorophenyl-propargylcarbinol | 92.9 | 90.6/9.4 | mp 44.5–45.5° C. | FD-MS 214(M$^+$) 216(M + 2$^+$) 218(M + 4$^+$) |
| Propargyl-2-thienylcarbinol | 90.4 | 91.0/9.0 | 1.559 (20° C.) | FI-MS 152(M$^+$) |
| 1-Propargylcyclo-hexan-1-ol | 92.9 | 100.0/0.0 | | |

TABLE 1-continued

| | | | | | |
|---|---|---|---|---|---|
| 4-Methyl-1-octyn-4-ol | 91.4 | " | | 1.446 (21° C.) | FI-MS 140(M+) |
| 3-Methyl-1-phenyl-5-hexyn-3-ol | 98.8 | " | | 1.525 (20° C.) | FD-MS 188(M+) |
| 5-Methyl-1-phenyl-hexan-1-en-5-yl-3-ol | 97.7 | " | | 1.567 (21° C.) | FD-MS 186(M+) |
| 2-Phenyl-4-pentyn-2-ol | 96.0 | " | | 1.537 (21° C.) | FI-MS 160(M+) |
| 5-Propargylnonan-5-ol | 96.6 | " | | 1.452 (21° C.) | FI-MS 182(M+) |

EXAMPLE 35

58.30 Grams of 2,3-dichloro-1-propene were added dropwise to a mixture of 30.00 g of heptanal, 90 g of toluene, 120 g of 5% acetic acid and 34.35 g of zinc powder at 45° C., and then the mixture was allowed to react at the same time temperature for 3 hours. After the reaction was completed zinc-derived insolubles were filtered off, and the resultant filtrate was subjected to separation. The organic phase was washed with a 7% sodium carbonate aqueous solution an dried over sodium sulfate. The desiccant was filtered off, and then the toluene was distilled off under reduced pressure to give 46.31 g of 2-chloroallyl-n-hexylcarbinol. The yield thereof was 92.4%.

EXAMPLE 36

40.00 Grams of 2-chloroallylphenylcarbionol were dissolved in 400 g of dimethylformamide, and 36.85 g of potassium hydroxide in a flake form were added. The mixture was stirred at room temperature for 2 hours and then neutralized with a 20% acetic acid aqueous solution. The resultant mixture was subjected to extraction with toluene. The toluene phase was washed with water and then dried over magnesium sulfate. The desiccant was filtered off, and the toluene was distilled off under reduced pressure to give 31.35 g of phenylpropargylcarbinol, $n_D^{20}=1.546$, FI-MS m/e 146 (M+), propargyl compound/allene compound=92.3/7.7.

EXAMPLE 37-52

Haloallylcarbinol compounds (II) were produced from aldehyde compounds (III-1) shown in Table 2 according to conditions described in Example 7. The results are shown in Table 2.

TABLE 2

| | Aldehyde (III-1) | | | Reaction temperature (°C.) | Reaction time (hr) | Haloallylcarbinol (II) | | | |
|---|---|---|---|---|---|---|---|---|---|
| Example | Name | Amount (g) | Organic solvent | | | Name | Yield (%) | mp (°C.) | bp (°C.) |
| 37 | Acetaldehyde | 30.00 | Ethyl ether | 32 | 3 | 2-Chloro-allylmethyl-carbinol | 97.6 | | 42 (5 mm Hg) |
| 38 | Propion-aldehyde | " | Ethyl ether | " | " | 2-Chloro-allylethyl-carbinol | 98.0 | | 54 (5 mm Hg) |
| 39 | 2-Methyl-propion-aldehyde | " | Ethyl ether | " | " | 2-Chloro-allylisopropylcarbinol | 99.7 | | 38-40 (5 mm Hg) |
| 40 | Pentanal | " | Toluene | 35 | 1.5 | Butyl-2-chloroallyl-carbinol | 98.9 | | 55-57 (3 mm Hg) |
| 41 | Hexanal | " | " | " | 2 | 2-Chloro-allylpentyl-carbinol | 99.0 | | 66 (3 mm Hg) |
| 42 | Cyclohexane-carbaldehyde | " | " | 45 | 3 | 2-Chloro-allylcyclohexylcarbinol | 95.7 | | 72-75 (0.5 mm Hg) |
| 43 | Citral | 30.00 | Toluene | 45 | 3 | 2-Chloroallyl-2',6'-dimethyl-1',5'-heptadienyl-carbinol | 95.7 | | 117-119 (0.8 mm Hg) |
| 44 | 2-Phenyl-propional- | " | " | " | " | 2-Chloro-allyl-1'-phenylethyl-carbinol | 94.9 | 48-56 | |
| 45 | Cinnamic aldehyde | " | " | " | " | 2-Chloro-allylstyryl-carbinol | 74.2 | | 132-134 (0.8 mm Hg) |
| 46 | p-Tolaldehyde | " | " | 35 | " | 2-Chloro-allyl-p-tolylcarbinol | 98.2 | | 96-98 (0.5 mm Hg) |
| 47 | p-Methoxy-benzaldehyde | " | " | " | " | 2-Chloro-allyl-p-methoxyphenyl carbinol | 96.0 | | 122-123 (0.6 mm Hg) |
| 48 | Piperonal | " | " | 45 | " | 2-Chloroallyl-3',4'-methyl-enedioxy- | 93.7 | 56-57 | |

TABLE 2-continued

| | | | | | phenylcarbinol | | |
|---|---|---|---|---|---|---|---|
| 49 | p-Chloro-benzaldehyde | 30.00 | Toluene | 45 | 3 | 2-Chloroallyl-p-chloro-phenylcarbinol | 95.0 | 48–50 |
| 50 | 2,4-Dichloro- | " | " | 35 | " | 2-Chloroallyl-2',4'-di-chlorophenyl-carbinol | 93.6 | 41 |
| 51 | m-Phenoxy-benzaldehyde | " | " | 45 | " | 2-Chloroallyl-m-phenoxy-phenylcarbinol | 96.4 | 169–170 (0.6 mm Hg) |
| 52 | 2-Thiophene-carbaldehyde | " | " | " | " | 2-Chloro-allyl-2'-thienyl-carbinol | 92.1 | 84–86 (0.9 mm Hg) |

| | | Haloallylcarbinol (II) | | |
|---|---|---|---|---|
| $n_D$ | MS | IR | $^1$H-NMR (CDCl3, internal standard TMS) | |
| 1.459 (25° C.) | FI-MS 120(M$^+$) 122(M + 2$^+$) | neat 3370 cm$^{-1}$ 1640 cm$^{-1}$ | δ1.25(d, 3H, J=7.1Hz), 1.91(brs, 1H), 2.39–2.54 (m, 2H), 4.15(m, 1H), 5.24(m, 1H), 5.27(d, 1H, J=1.3Hz) | |
| 1.457 (25° C.) | FI-MS 134(M$^+$) 136(M + 2$^+$) | neat 3380 cm$^{-1}$ 1640 cm$^{-1}$ | δ0.98(t, 3H, J=7.1Hz), 1.45–1.61(m, 2H), 1.82 (brs, 1H), 2.39–2.53(m, 2H), 3.82–3.91(m, 1H), 5.25 (m, 1H), 5.27(d, 1H, J=1.3Hz) | |
| 1.459 (20° C.) | FI-MS 148(M$^+$) 150(M + 2$^+$) | neat 3420 cm$^{-1}$ 1640 cm$^{-1}$ | δ0.96(d, 6H, J=6.9Hz), 1.68–1.80(m, 2H), 2.36–2.53 (m, 2H), 3.72(ddd, 1H, J=8.9, 5.3, 3.6Hz), 5.26(dt, 1H, J=1.3, 0.7Hz), 5.29(d, 1H, J=1.3Hz) | |
| 1.459 (25° C.) | FD-MS 163(M + H$^+$) 165(M + H + 2$^+$) | neat 3380 cm$^{-1}$ 1640 cm$^{-1}$ | δ0.93(t, 3H, J=7.0Hz), 1.29–1.54(m, 6H), 1.74 (brs, 1H), 2.34–2.52(m, 2H), 3.93(m, 1H), 5.25(m, 1H), 5.27(d, 1H, J=1.3Hz) | |
| 1.459 (25° C.) | FD-MS 177(M + H$^+$) 179(M + H + 2$^+$) | neat 3380 cm$^{-1}$ 1640 cm$^{-1}$ | δ0.89(m, 3H), 1.25–1.50(m, 8H), 1.76(brs, 1H), 2.36–2.55(m, 2H), 3.92(m, 1H), 5.24(m, 1H), 5.29 (d, 1H, J=1.3Hz) | |
| 1.490 (19° C.) | FI-MS 188 (M$^+$), 190(M + 2$^+$) 170(M – H$_2$O$^+$) 172(M – H$_2$O + 2$^+$) | neat 3400 cm$^{-1}$ 1635 cm$^{-1}$ | δ0.99–1.45(m, 6H), 1.67–1.85(m, 6H), 2.37–2.55(m, 2H), 3.71(dt, 1H, J=3.6, 9.1Hz), 5.25(m, 1H), 5.29 (d, 1H, J=1.3Hz) | |
| 1.4919 (21° C.) | FD-MS 228(M$^+$) 230(M + 2$^+$) | neat 3370 cm$^{-1}$ 1640 cm$^{-1}$ | δ1.60–1.75(m, 10H), 1.98–2.20(m, 4H), 2.38–2.47 (m, 1H), 2.52–2.63(m, 1H), 4.72(m, 1H), 5.05–5.21 (m, 2H), 5.23(m, 1H), 5.26(d, 1H, J=1.0Hz) | |
| | FD-MS 210(M$^+$) 212(M + 2$^+$) | KBr method 3420 cm$^{-1}$ 1640 cm$^{-1}$ | δ1.36(d, 3H, J=6.9Hz), 1.84(brs, 1H), 2.28–2.40 (m, 2H), 2.80(quint, 1H, J=6.9Hz), 4.03(ddd, 1H, 1H), J=1.3Hz), 7.19–7.35(m, 5H) | |
| 1.5761 (19° C.) | FD-MS 208(M$^+$) 210(M + 2$^+$) | neat 3400 cm$^{-1}$ 1640 cm$^{-1}$ | δ2.10(brs, 1H), 2.55–2.70(m, 2H), 4.63(m, 1H), 5.27(m, 1H), 5.30(d, 1H, J=1.3Hz), 6.21(dd, 1H, J=15.8, 6.6Hz), 6.65(dd, 1H, J=15.8, 1.0Hz), 7.18–7.57(m, 5H) | |
| 1.5338 (25° C.) | FD-MS 196(M$^+$) 198(M + 2$^+$) | neat 3400 cm$^{-1}$ 1640 cm$^{-1}$ | δ2.21(brs, 1H), 2.33(s, 3H), 2.56–2.77(m, 2H), 4.95(dd, 1H, J=9.0, 4.9Hz), 5.19(m, 1H), 5.24(d, 1H, J=1.3Hz), 7.11–7.23(m, 4H) | |
| 1.5455 (25° C.) | FD-MS 212(M$^+$) 214(M + 2$^+$) | neat 3430 cm$^{-1}$ 1640 cm$^{-1}$ | δ1.97(brs, 1H), 2.59–2.81(m, 2H), 3.80(s, 3H), 4.98(dd, 1H, J=8.7, 5.2Hz), 5.20(m, 1H), 5.26(d, 1H, J=1.3Hz), 6.88(m, 2H), 7.28(m, 2H) | |
| | FD-MS 226(M$^+$) 228(M + 2$^+$) | KBr method 3380 cm$^{-1}$ 1640 cm$^{-1}$ | δ2.11(d, 1H, J=2.6Hz), 2.57–2.79(m, 2H), 4.94(m, 1H), 5.22(m, 1H), 5.27(d, 1H, J=1.3Hz), 5.95(s, 2H), 6.75–6.89(m, 3H) | |
| | FD-MS 216(M$^+$) 218(M + 2$^+$) 220(M + 4$^+$) | KBr method 3390 cm$^{-1}$ 1635 cm$^{-1}$ | δ2.28(d, 1H, J=3.3Hz), 2.57–2.77(m, 2H), 4.99(m, 1H), 5.20(m, 1H), 5.27(d, 1H, J=1.3Hz), 7.31(s, 4H) | |
| | FD-MS 250(M$^+$) 252(M + 2$^+$) 254(M + 4$^+$) | KBr method 3420 cm$^{-1}$ 1635 cm$^{-1}$ | δ2.34(s, 1H), 2.44–2.56(m, 2H), 5.29(m, 1H), 5.33 (d, 1H, J=1.3Hz), 5.43(m, 1H), 7.08–7.27(m, 3H) | |
| 1.5804 (25° C.) | FD-MS 274(M$^+$) 276(M + 2$^+$) | neat 3410 cm$^{-1}$ 1635 cm$^{-1}$ | δ2.17(brs, 1H), 2.60–2.78(m, 2H), 4.99(dd, 1H), J=8.6, 4.6Hz), 5.21(m, 1H), 5.28(d, 1H, J=1.0Hz), 6.89–7.37(m, 9H) | |
| 1.5585 (19° C.) | FI-MS 170(M – H$_2$O$^+$) 172(M – H$_2$O + 2$^+$) | neat 3390 cm$^{-1}$ 1640 cm$^{-1}$ | δ2.39(d, 1H, J=3.3Hz), 2.73–2.92(m, 2H), 5.25–5.31 (m, 3H), 6.98(m, 2H), 7.25(dd, 1H, J=5.0, 1.3Hz) | |

EXAMPLE 53

56.53 Grams of 2,3-dichloro-1-propene were added dropwise to a mixture of 25.00 g of cyclohexanone, 75 g of toluene, 100 g of 5% acetic acid and 34.35 g of zinc powder at 45° C., and then the mixture was allowed to react at the same temperature for 3 hours. After the reaction was completed zinc-derived insolubles were filtered off, and the resultant filtrate was subjected to separation. The organic phase was washed with a 7% sodium carbonate aqueous solution and dried over sodium sulfate. The desiccant was filtered off, and then the toluene was distilled off under reduced pressure to give 44.05 g of 1-(2'-chloroallyl)-1-cyclohexanol. The results were as follows.

Yield 99.0%.
bp 62-65° C./0.5 mmHg.
$n_D^{20}$ 1.4950.
FI-MS m/e 156 (M-$H_2O^+$), 158 (M-$H_2O$+2$^+$).
IR (neat) 3460, 1630 cm$^{-1}$.
$^1$H-NMR (CDCl$_3$, internal standard TMS), δ1.26-1.71 (m, 10H), 1.82 (s, 1H), 2.54 (s, 2H), 5.21 (d, 1H, J=0.8 Hz), 5.34 (d, 1H, J=0.8 Hz).

EXAMPLES 54-65

Haloallylcarbinol compounds (II) were produced from ketone compounds (III-2) shown in Table 3 according to the conditions described in Example 53. The results are shown in Table 3.

TABLE 3

| Example | Ketone (III-2) Name | Amount (g) | Organic solvent Name | Amount (g) | Acetic acid Concentration (%) | Amount (g) | Amount of 2,3-dichloro-1-propene (g) | Amount of zinc (g) | Reaction temperature (°C.) | Reaction time (hr) |
|---|---|---|---|---|---|---|---|---|---|---|
| 54 | Methyl n-butyl ketone | 10.00 | Toluene | 30 | 5 | 40 | 22.15 | 13.05 | 45 | 5.5 |
| 55 | Methyl n-butyl ketone | " | None | 0 | " | " | " | " | " | 3 |
| 56 | Methyl n-butyl ketone | " | " | " | 10 | " | 33.23 | 19.58 | " | " |
| 57 | Methyl 2-phenylethyl ketone | 20.00 | Toluene | 60 | 5 | 80 | 29.96 | 17.65 | 45 | 5 |
| 58 | Methyl 2-phenylethyl ketone | 20.00 | Toluene | 60 | 5 | 80 | 59.92 | 35.30 | 45 | 2 |
| 59 | Methyl 2-phenylethyl ketone | " | " | " | " | " | 89.88 | 52.95 | " | " |
| 60 | Benzalacetone | 30.00 | " | 90 | " | 120 | 45.54 | 26.83 | " | " |
| 61 | Benzalacetone | " | " | " | " | " | 136.62 | 80.49 | " | " |
| 62 | Acetophenone | 30.00 | Toluene | 90 | 5 | 120 | 55.42 | 32.65 | 45 | 2 |
| 63 | Acetophenone | " | " | " | " | " | 110.84 | 65.30 | " | " |
| 64 | Acetophenone | " | " | " | " | " | 166.26 | 97.95 | " | " |
| 65 | di-n-Butyl ketone | " | None | 0 | 10 | " | 210.65 | 124.11 | " | " |

| Name | tertiary Haloallylcarbinol (II) Yield (%) | mp (°C.) | bp (°C.) | $n_D$ | MS | IR | $^1$H-NMR (CDCl$_3$, internal standard TMS) |
|---|---|---|---|---|---|---|---|
| 2-Chloro-4-methyl-1-octen-4-ol | 52.2 | | 54-56 (5 mm Hg) | 1.461 (20° C.) | FI-MS 177(M + H$^+$) 179(M + H + 2$^+$) 158(M − $H_2O^+$) 160(M − $H_2O$ + 2$^+$) | neat 3450 cm$^{-1}$ 1630 cm$^{-1}$ | δ0.92(m, 3H), 1.25(s, 3H), 1.32-1.57(m, 6H), 1.86(brs, 1H), 2.54(m, 2H), 5.22(d, 1H, J=1.0Hz), 5.35(d, 1H, J=1.0Hz) |
| 2-Chloro-4-methyl-1-octen-4-ol | 77.3 | | | | | | |
| 2-Chloro-4-methyl-1-octen-4-ol | 94.0 | | | | | | |
| 5-Chloro-3-methyl-1-phenyl-5-hexen-3-ol | 29.9 | 126-128 | (0.9 mm Hg) | 1.530 (21° C.) | FI-MS 206(M − $H_2O^+$) 208(M − $H_2O$ + 2$^+$) | neat 3470 cm$^{-1}$ 1640 cm$^{-1}$ | δ1.33(s, 3H), 1.82-1.88 (m, 3H), 2.61(d, 2H, J=4.0Hz), 2.70-2.79(m, 2H), 5.24(m, 1H), 5.37 d, 1H, J=1.3Hz), 7.15-7.32(m, 5H) |
| 5-Chloro-3-methyl-1-phenyl-5-hexen-3-3-ol | 59.5 | | | | | | |
| 5-Chloro-3-methyl-1-phenyl-5-hexen-3- | 93.1 | | | | | | |

TABLE 3-continued

| | | | | | | |
|---|---|---|---|---|---|---|
| 3-ol | | | | | | |
| 5-Chloro-3-methyl-1-phenyl-1,5-hexadien-3-ol | 27.1 | | 1.5648 (19° C.) | FD-MS 222(M+) 224(M + 2+) | neat 3440 cm⁻¹ 1630 cm⁻¹ | δ1.46(s, 3H), 1.68(s, 1H), 2.70(s, 2H), 5.25 (d, 1H, J=1.0Hz), 5.35 (d, 1H, J=1.0Hz), 6.33 (d, 1H, J=15.8Hz), 6.65 (d, 1H, J=15.8Hz), 7.09-7.43(m, 5H) |
| 5-Chloro-3-methyl-1-phenyl-1,5-hexadien-3-ol | 78.8 | | | | | |
| 4-Chloro-2-phenyl-4-penten-2-ol | 42.4 | 84-85 (0.5 mm Hg) | 1.5395 (20° C.) | FI-MS 178(M − H₂O⁺) 180(M − H₂O + 2⁺) | neat 3460 cm⁻¹ 1635 cm⁻¹ | δ1.64(s, 3H), 2.37(brs, 1H), 2.82(d, 1H, J=14.7Hz), 2.91(d, 1H, J=14.7Hz), 5.07(d, 1H, 1.3Hz), 5.27(d, 1H, J=1.3Hz), 5.27(d, 1H, J=1.3Hz), 7.22-7.47(m, 5H) |
| 4-Chloro-2-phenyl-4-penten-2-ol | 71.5 | | | | | |
| 4-Chloro-2-phenyl-4-penten-2-ol | 93.7 | | | | | |
| 5-(2'-chloro-allyl)-nonan-5-ol | 59.2 | 77-79 (0.5 mm Hg) | 1.4613 (19° C.) | FI-MS 200(M − H₂O⁺) 202(M − H₂O + 2⁺) | neat 3480 cm⁻¹ 1630 cm⁻¹ | δ0.91(m, 6H), 1.32(m, 8H), 1.51(m, 4H), 1.78 (s, 1H), 2.53(s, 2H), 5.21(d, 1H, J=1.0Hz), 5.34(d, 1H, 1.0Hz) |

What is claimed is:

1. A process for producing a propargylcarbinol compound of the formula (I):

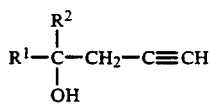

$$R^1-\underset{\underset{OH}{|}}{\overset{\overset{R^2}{|}}{C}}-CH_2-C\equiv CH \quad (I)$$

where $R^1$ and $R^2$ independently represent hydrogen; $C_1$-$C_{15}$ alkyl which is unsubstituted or substituted with at least one member selected from the group consisting of halogen, hydroxy, phenyl, phenoxy, and phenyl or phenoxy which is substituted with at least one member selected from the group consisting of halogen, hydroxyl, alkoxy, phenoxy, dialkylamino and methylenedioxy, aralkyloxy, dialkylamino, alkylthio, phenylthio, biphenyl and phenylalkyl; $C_2$-$C_{15}$ alkenyl which is unsubstituted or substituted with at least one member selected from the group consisting of halogen, hydroxyl, phenyl, phenoxy, and phenyl or phenoxy which is substituted with at least one member selected from the group consisting of halogen, hydroxyl, alkoxy, phenoxy, dialkylamino and methylenedioxy, dialkylamino, alkylthio, phenylthio, biphenyl and phenylalkyl; $C_2$-$C_{15}$ alkynyl which is unsubstituted or substituted with at least one member selected from the group consisting of halogen, hydroxyl, phenyl, phenoxy, and phenyl or phenoxy which is substituted with at least one member selected from the group consisting of halogen, hydroxyl, alkoxy, phenoxy, dialkylamino and methylenedioxy, dialkylamino, alkylthio, phenylthio, biphenyl and phenylalkyl; $C_3$-$C_{15}$ cycloalkyl; $C_4$-$C_{15}$ cycloalkenyl; or phenyl, naphthyl, furyl or thienyl which is unsubstituted or substituted with at least one member selected from the group consisting of halogen, hydroxyl, alkyl, alkoxy, phenoxy, dialkylamino and methylenedioxy; or $R^1$ and $R^2$ together represent $C_2$-$C_{15}$ alkenylene or alkenylene chain; with the proviso that the carbon atoms in the 1-positions of $R^1$ and $R^2$ do not together form tertiary carbon atoms and that when one of $R^1$ and $R^2$ is furyl, the other does not represent hydrogen:

which comprises reacting a haloallylcarbinol compound of the formula (II):

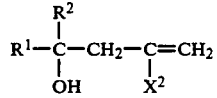

$$R^1-\underset{\underset{OH}{|}}{\overset{\overset{R^2}{|}}{C}}-CH_2-\underset{\underset{X^2}{|}}{C}=CH_2 \quad (II)$$

wherein $R^1$ and $R^2$ are as defined above and $X^2$ represents chlorine, bromine or iodine, with a base at 0-60° C.

2. A process according to claim 1, wherein the haloallylcarbinol compound is reacted with an alkali metal hydroxide in the presence of a polar aprotic solvent.

3. A process according to claim 1, wherein the haloallylcarbinol compound is reacted with an alkali metal hydroxide in the presence of a diamine.

4. A process according to claim 1, wherein the haloallylcarbinol compound is reacted with an alkali metal alkoxide in the presence of a diamine.

5. A process according to claim 3 or 4, wherein the diamine is selected from the group consisting of ethylenediamine, N,N,N',N'-tetramethylethylenediamine, 1,2-diaminopropane, 1,3-diaminopropane, 1,8-diazabicyclo[5,4,0]undec-7-ene, 1,5-diazabicyclo[4,3,0]-non-5-ene, and 1,4-diazabicyclo[2,2,2]octane.

6. A process according to claim 1, wherein the haloallylcarbinol compound is reacted with an alkali metal hydroxide in the presence of a phase transfer catalyst in one solvent selected from the group consisting of a mixed solvent of hydrophobic hydrocarbon with water, a mixed solvent of hydrophobic hydrocarbon halide with water and water.

7. A process according to claim 1, wherein the haloallylcarbinol compound is reacted with an alkali metal alkoxide in the presence of a polar aprotic solvent.

8. A process according to claim 2 or 7, wherein the polar aprotic solvent is selected from the group consisting of acetonitrile, N,N-dimethylacetamide, N,N-dimethylformamide, N-methyl-2-pyrrolidone, and dimethylsulfoxide.

9. A process according to claim 1 including the further steps of providing the compound of formula (II) by reacting a carbonyl compound of the formula (III):

where $R^1$ and $R^2$ are as defined in claim 1, with a dihalopropene compound of the formula (IV):

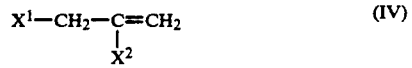

where $X^1$ and $X^2$ independently represent chlorine, bromine or iodine, in the presence of zinc and water to obtain the haloallylcarbinol compound of the formula (II).

10. A process according to claim 9, wherein the dihalopropene compound is a dichloropropene compound.

11. A process according to any one of claims 1 to 4, 6, 7 or 9, wherein each of $R^1$ and $R^2$ independently represents hydrogen, $C_1$–$C_{15}$ alkyl which is unsubstituted or substituted with at least one member selected from the group consisting of halogen, hydroxy, phenyl, phenoxy, aralkyloxy, dialkylamino, alkylthio, phenylthio, biphenyl and phenylalkyl; $C_3$–$C_9$ cycloalkyl or cycloalkenyl; $C_2$–$C_9$ alkenyl which is unsubstituted or substituted with phenyl; $C_2$–$C_6$ alkynyl; or phenyl, naphthyl, furyl or thienyl which is unsubstituted or substituted with at least one member selected from the group consisting of halogen, hydroxyl, alkyl, alkoxy, phenoxy, dialkylamino and methylenedioxy.

12. A process according to claim 5, wherein each of $R^1$ and $R^2$ independently of the other represents hydrogen, $C_1$–$C_{15}$ alkyl which in unsubstituted or substituted with at least one member selected from the group consisting of halogen, hydroxy, phenyl, phenoxy, aralkyloxy, dialkylamino, alkylthio, phenylthio, biphenyl and phenylalkyl; $C_3$–$C_9$ cycloalkyl or cycloalkenyl; $C_2$–$C_9$ alkenyl which is unsubstituted or substituted with phenyl; $C_2$–$C_6$ alkynyl; or phenyl, naphthyl, furyl or thienyl which is unsubstituted or substituted with at least one member selected from the group consisting of halogen, hydroxyl, alkyl, alkoxy, phenoxy, dialkylamino and methylenedioxy.

13. A process according to claim 8, wherein each of $R^1$ and $R^2$ independently of the other represents hydrogen, $C_1$–$C_{15}$ alkyl which in unsubstituted or substituted with at least one member selected from the group consisting of halogen, hydroxy, phenyl, phenoxy, aralkyloxy, dialkylamino, alkylthio, phenylthio, biphenyl and phenylalkyl; $C_3$–$C_9$ cycloalkyl or cycloalkenyl; $C_2$–$C_9$ alkenyl which is unsubstituted or substituted with phenyl; $C_2$–$C_6$ alkynyl; or phenyl, naphthyl, furyl or thienyl which is unsubstituted or substituted with at least one member selected from the group consisting of halogen, hydroxyl, alkyl, alkoxy, phenoxy, dialkylamino and methylenedioxy.

14. A process according to claim 11, wherein each of $R^1$ and $R^2$ independently of the other represents hydrogen, $C_1$–$C_{15}$ alkyl which in unsubstituted or substituted with at least one member selected from the group consisting of halogen, hydroxyl, phenyl, phenoxy, aralkyloxy, dialkylamino, alkylthio, phenylthio, biphenyl and phenylalkyl; $C_3$–$C_9$ cycloalkyl or cycloalkenyl; $C_2$–$C_9$ alkenyl which is unsubstituted or substituted with phenyl; $C_2$–$C_6$ alkynyl; or phenyl, naphthyl, furyl or thienyl which is unsubstituted or substituted with at least one member selected from the group consisting of halogen, hydroxyl, alkyl, alkoxy, phenoxy, dialkylamino and methylenedioxy.

15. A process according to any one of claims 1 to 4, 6, 7 or 9, wherein each of $R^1$ and $R^2$ independently of the other represents $C_1$–$C_{15}$ alkyl which is unsubstituted or substituted with phenyl; $C_2$–$C_9$ alkenyl which is unsubstituted or substituted with phenyl; $C_5$–$C_7$ cycloalkyl or cycloalkenyl; phenyl, naphthyl or thienyl which is unsubstituted or substituted with at least one member selected from the group consisting of halogen, $C_1$–$C_3$ alkyl, $C_1$–$C_3$ alkoxy, phenoxy and methylenedioxy; or hydrogen.

16. A process according to claim 5, wherein each of $R^1$ and $R^2$ independently of the other represents $C_1$–$C_{15}$ alkyl which is unsubstituted or substituted with phenyl; $C_2$–$C_9$ alkenyl which is unsubstituted or substituted with phenyl; $C_5$–$C_7$ cycloalkyl or cycloalkenyl; phenyl, naphthyl or thienyl which is unsubstituted or substituted with at least one member selected from the group consisting of halogen, $C_1$–$C_3$ alkyl, $C_1$–$C_3$ alkoxy, phenoxy and methylenedioxy; or hydrogen.

17. A process according to claim 8, wherein each of $R^1$ and $R^2$ independently of the other represents $C_1$–$C_{15}$ alkyl which is unsubstituted or substituted with phenyl; $C_2$–$C_9$ alkenyl which is unsubstituted or substituted with phenyl; $C_5$–$C_7$ cycloalkyl or cycloalkenyl; phenyl, naphthyl or thienyl which is unsubstituted or substituted with at least one member selected from the group consisting of halogen, $C_1$–$C_3$ alkyl, $C_1$–$C_3$ alkoxy, phenoxy and methylenedioxy; or hydrogen.

18. A process according to claim 10, wherein each of $R^1$ and $R^2$ independently of the other represents $C_1$–$C_{15}$ alkyl which is unsubstituted or substituted with phenyl; $C_2$–$C_9$ alkenyl which is unsubstituted or substituted with phenyl; $C_5$–$C_7$ cycloalkyl or cycloalkenyl; phenyl, naphthyl or thienyl which is unsubstituted or substituted with at least one member selected from the group consisting of halogen, $C_1$–$C_3$ alkyl, $C_1$–$C_3$ alkoxy, phenoxy and methylenedioxy; or hydrogen.

* * * * *